United States Patent
Fresco et al.

(10) Patent No.: US 6,783,932 B2
(45) Date of Patent: Aug. 31, 2004

(54) STABILIZATION OF TRIPLEXES BY WATER STRUCTURE-MAKING SUBSTANCES

(75) Inventors: Jacques R. Fresco, Princeton, NJ (US); John Laurence Richard Lavelle, Los Angeles, CA (US)

(73) Assignee: Princeton University, Princeton, NJ (US)

(*) Notice: Subject to any disclaimer, the term of this patent is extended or adjusted under 35 U.S.C. 154(b) by 57 days.

(21) Appl. No.: 09/341,079

(22) PCT Filed: Jan. 2, 1998

(86) PCT No.: PCT/US98/00246
§ 371 (c)(1),
(2), (4) Date: Jul. 2, 1999

(87) PCT Pub. No.: WO98/29428
PCT Pub. Date: Jul. 9, 1998

(65) Prior Publication Data
US 2002/0137919 A1 Sep. 26, 2002

Related U.S. Application Data

(60) Provisional application No. 60/034,592, filed on Jan. 2, 1997.

(51) Int. Cl.[7] .......................... C12Q 1/68; C12P 19/34; C12N 15/11
(52) U.S. Cl. .......................... 435/6; 435/91.1; 536/23.1
(58) Field of Search .................... 435/6, 91.1; 536/23.1

(56) References Cited

U.S. PATENT DOCUMENTS

| | | | |
|---|---|---|---|
| 5,422,251 A | 6/1995 | Fresco | 435/91.1 |
| 5,474,911 A | 12/1995 | Pontius | 435/41 |
| 5,521,061 A | 5/1996 | Bresser et al. | 435/5 |
| 5,693,471 A | 12/1997 | Fresco | 435/6 |

OTHER PUBLICATIONS

Moser et al., Sequence–Specific Cleavage of Double Helical DNA by Triple Helix Formation, Research Articles, Science, vol. 238 Oct. 30, 1987, p. 645–650.*

Spink et al., Selective Stabilization of Triplex DNA by Poly(ethylene glycols), J. Am. Chem. Soc. 1995, 117, 12887–12888.*

Kim HK et al, "Interactions of intercalative and minor groove binding ligands with triplex poly(dA).poly(dT)2 and with duplex . . . ", Biochemistry, Jan. 30, 1996, vol. 35, No. 4, pp. 1187–1194.*

Kiyama R et al., "Protection of DNA sequences by triplex–bridge formation", Nucleic Acids Research, Feb. 11, 1995, vol. 23, No. 3, pp. 452–458.*

D'Souza DJ et al, "Solvent pH, and ionic effects on the binding of single–stranded DNA by circular oligodeoxy-nucleotides", Bioorganic and Medicinal Chemistry Letters, vol. 4, No. 8, 1994, pp. 965–970.*

Robles J et al, "A parallel–stranded DNA triplex tethering a Hoeschst 33258 analogue results in complex stabilization by siumultaneous major groove and minor groove binding", J Am Chem Soc, Jun. 19, 1996, vol. 118, pp. 5820–5821.*

Shimizu M et al, "Detailed study of sequence–specific DNA cleavage of triplex–forming oligonucleotides linked to 1, 10–phenanthroline", Biochemistry, Jan. 18, 1994, vol. 33, No. 2, pp. 606–613.*

"Analytical Strategies for othe Use of DNA Probes" by J.A. Matthews and L.J. Kricka; Analytical Bio–chemistry 169; pp. 1–25 (Feb. 1988).

* cited by examiner

*Primary Examiner*—John S. Brusca
(74) *Attorney, Agent, or Firm*—Rothwell, Figg, Ernst & Manbeck, PC

(57) ABSTRACT

The stability of a triplex in solution is enhanced by adding to the solution, either before or after formation of the triplex, an effective amount of either of the following: (a) a water structure-making substance, at an appropriately high concentration, other than an alkali or alkaline earth metal cation, a tetramethylammonium cation, or a polyamine; or (b) a combination of said water structure-making substance and an alkali or alkaline earth cation or a tetramethylammonium cation or a polyamine.

32 Claims, No Drawings

US 6,783,932 B2

STABILIZATION OF TRIPLEXES BY WATER STRUCTURE-MAKING SUBSTANCES

CROSS REFERENCE TO RELATED APPLICATIONS

This application claims the benefit of U.S. Provisional Application No. 60/034,592 filed Jan. 2, 1997.

STATEMENT REGARDING FEDERALLY SPONSORED RESEARCH OR DEVELOPMENT

The United States Government may have certain rights in this invention by virtue of NIH Grant GM42936 and NIH Biophysics Training Grant GM08309.

BACKGROUND OF THE INVENTION

1. Field of the Invention

The invention relates to methods for stabilizing nucleic acid triplexes.

2. Description of Related Art

Oligonucleotide third strands can bind to double-stranded nucleic acids to form triple-stranded helices (triplexes) in a sequence specific manner. The third strand binding code (a complementarity principle) dictates the sequence specificity for binding third strands in the major groove of double-stranded nucleic acids to form a triple-stranded helix or triplex. The code provides the specificity of third-strand binding for design of gene-based therapeutic agents that bind specifically to target nucleic acid sequences with little or no non-specific binding to non-target sequences. The third strand binding code, as well as various utilities for triplexes, are described in U.S. Pat. Nos. 5,422,251 and 5,693,471 to Fresco, which also shows ionic conditions such as the presence of $Mg^{+2}$, $Mn^{+2}$, $Ca^{+2}$, $Na^+$, $Li^+$, $K^+$ or tetramethylammonium cations suitable for triplex formation.

SUMMARY OF THE INVENTION

The present invention relates to methods for enhancing the stability of a triplex formed from one or more nucleic acid strands in a solution, said method comprising adding to the solution, either before or after formation of the triplex, an effective amount of either of the following:

(a) a water structure-making substance other than an alkali or alkaline earth metal cation, a tetramethylammonium cation, or a polyamine; or (b) a combination of said water structure-making substance and an alkali or alkaline earth metal cation a tetramethylammonium cation, or a polyamine.

The present invention further relates to a method for forming a triplex from one or more nucleic acid strands, said method comprising adding to a solution, in any order, the strand(s) and an effective amount of one of the following:

(a) a water structure-making substance other than an alkali or alkaline earth metal cation, a tetramethylammonium cation, or a polyamine; or (b) a combination of said water structure-making substance and an alkali or alkaline earth metal cation, a tetramethylammonium cation, or a polyamine; and allowing said triplex to form.

DETAILED DESCRIPTION OF THE INVENTION

As mentioned above, it has been discovered that water structure-making substances can stabilize triplexes in solution. By water structure-making substance is meant a substance which, when dissolved in water, will yield ions or other structures which interact with water more strongly than bulk water molecules with each other.

The water structure-making substances include organic cations, cationic lipids, organic anions, inorganic anions, and water-miscible organic solvents. Preferred organic cations include alkylammonium (e.g., methylammonium, dimethylammonium, trimethylammonium, tetramethylammonium, and tetraethylammonium, triethylammonium, and their derivatives). Preferred cationic lipids include cetyltrimethylammonium, tridodecylmethylammonium, and 2,3-dioleyloxy-N-[2 (sperminecarboxamido)ethyl]-N,N-dimethyl-1-propanammonium and their derivatives. Preferred organic anions include acetate and its derivatives. Preferred inorganic anions include phosphate, sulfate, etc., termed kosmotropes below. Preferred organic solvents include DMSO and alcohols, most preferably methanol, ethanol, 2-propanol, isopropanol and their derivatives.

The oligonucleotide third strand is a synthetic or natural oligonucleotide capable of binding with specificity to a predetermined target region of a double-stranded native nucleic acid molecule to form a triple-stranded structure. The third strand may bind solely to one strand of the native nucleic acid molecule, or may bind to both strands at different points along its length. The third strand need not be perfectly complementary to the duplex, but may be substantially complementary. In general, by substantially complementary is meant that one mismatch is tolerable in about every 10 base pairs.

The oligonucleotide may have a native phosphodiester backbone or may be comprised of other backbone chemical groups or mixtures of chemical groups which do not prevent a triple-stranded helix from forming. These alternative chemical groups include phosphorothioates, methylphosphonates, peptide nucleic acids (PNAs), and others known to those skilled in the art. Preferably, the oligonucleotide backbone is phosphodiester.

The oligonucleotide may also comprise one or more modified sugars, which would be known to those skilled in the art. As an example, such a sugar can be an α-enantiomer.

The third strand may also incorporate one or more unnatural (for nucleic acids) heterocycle base substitutes if such is necessary or desirable to improve third strand binding. Examples of such unnatural heterocycle design and the heterocycles so designed are found in the co-pending U.S. application of Fresco, et al. entitled "Residues for Binding Third Strands to Complementary Nucleic Acid Duplexes of any Base-Pair Sequence", Ser. No. 08/473,888 filed Jun. 7, 1995, the contents of which are incorporated herein by reference.

The third strand may also contain one or more of a variety of other substituents which can strengthen third strand binding to the target duplex. These include intercalators, crosslinkers, peptides, oligosaccharides, and their analogs and/or derivatives While the triplex is preferably formed from three discrete strands (two strands which form the duplex target via Watson-Crick binding, and a third strand probe), the present invention also encompasses stabilization of triplexes formed from less than three discrete strands. For example, the triplex may be formed from a single stranded target, and a probe strand that has a sequence complementary to the target strand to form the target duplex, as well as a sequence at a different position which will bind to the formed duplex as if it were a third strand. Further, the triplex may be formed from a target duplex which comprises a single strand which hybridizes to itself via a hairpin turn, and a third strand probe. The triplex may also be formed from a single strand which forms a triplex by virtue of two hairpin turns.

The order of addition of the components of the invention is not critical. For example, the water structure making substance(s) may be added to a solution which already contains the triplex to be stabilized, or may be added along with one or more strands. Moreover, the water structure-making substance may be covalently linked to the third strand in a manner which would be readily apparent to one of ordinary skill.

The term "solution" as used herein is intended to include both in vitro and in vivo environments. When dealing with in vivo solutions (i.e., in a cell), it will be recognized that toxicity concerns will affect the nature and concentration of water structure making substances that can be employed. In general, cationic lipids will be preferred when dealing with in vivo solutions, and may be formulated with the third strand for cellular uptake in a manner known to those of ordinary skill.

The optimum concentration of water structure-making substance to be added may readily be determined by one of ordinary skill). Appropriate concentrations for many substances are set forth in the examples and tables infra.

While not wishing to be bound by any particular theory of how the present invention works, it is known that when a salt is dissolved in water, different anions and cations are observed to decrease, increase or have little effect on the volume of the solution. These alternative effects have been explained in terms of the interaction of the anion or cation with water molecules according to what is often called the multilayer hydration model. Briefly, this model of ion-water interaction divides the volume of an ion in solution, $V_{ion}$, into four components:

$$V_{ion}=V_{cryst}+V_{elect}+V_{disord}+V_{caged}$$

where: $V_{cryt}$ is the volume of the ion based on its crystal radius; $V_{elect}$ is the electrostriction volume (stronger ion-$H_2O$ interaction decreases volume); $V_{disord}$ is the disordered or void-space volume (weaker ion-$H_2O$ interaction increases volume); and $V_{caged}$ is the caged or structured volume (that occurs when a hydrophobic ion (organic cation) interacts with $H_2O$ molecules, which decreases volume).

Although these ion volume factors are interdependent, the observed solution volume changes on addition of ions is readily explained by this descriptive model. Using this model, ions can be divided into three classes: 1) electrostrictive "structure-making" ions when $V_{elect}$ is dominant; 2) disordered "structure-breaking" ions when $V_{disord}$ is dominant; and 3) hydrophobic "structure-making" ions when $V_{caged}$ is dominant.

The volumes, $V_{elect}$, $V_{disord}$ and $V_{caged}$ have been calculated for a number of anions and cations (see Horne, R. A. (Ed.)(1972) *Water and Aqueous Solutions*, Wiley-Interscience, NY). As these volumes are additive, predictions of the solution volume effect of a particular salt can be made. The structure-making or structure-breaking tendency of anions based upon this model follows the rank order of the Hofmeister series, which is the relative tendency of anions to stabilize and solubilize proteins. A partial rank order is:

(destabilize proteins) $ClO_4^- < Cl^- < CH_3COO^- < HPO_4^{2-} < SO_4^{2-}$ (stabilize proteins)

This rank order is also known as the "chaotropic series", as studies have shown $Cl^-$ to have little effect on water-structure, whereas anions to the left of $Cl^-$ are water structure-breakers ($V_{disord}$ is dominant) called chaotropes (from the Greek, meaning disorder (chao)) because they destabilize proteins, while anions to the right of $Cl^-$ are water structure-makers ($V_{elect}$ is dominant) called kosmotropes (from the Greek, meaning order (kosmos)) because they stabilize proteins. Thus, polar or charged chaotropes "disrupt" the structure of water because they interact with water less strongly, while polar or charged kosmotropes interact with water more strongly than bulk water molecules with each other.

Previous work has shown that the effect of various salts on the stability of duplex DNA also follows the Hofmeister series (Hamaguchi and Geiduschek, *JACS* 84 (8), 1329–38 (1962)). In the same study it was concluded that at the very high concentrations needed to observe the anion effects, there were only minor differences observed when the cations $Li^+$, $Na^+$, $K^+$, and $TMA^+$ were varied.

The results obtained in accordance with the present invention show that the effect of anions on triplex stability follows the Hofmeister series. For the triplex $d(C^+-T)_6:d(A-G)_6\cdot d(C-T)_6$ in 2.0 M anion at pH 7.0, rank according to triplex Tm values (° C.) for the various salts is:

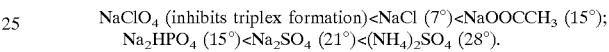

For the triplex $d(T)_{21}:d(A)_{21}\cdot d(T)_{21}$ in 2.0 M anion at pH 7.0, rank according to triplex Tm values (° C.) for the various salts is:

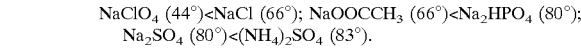

Whereas duplex DNA stability is not greatly affected by cations in general when they are at very high concentration, the applicants have found that organic cations have a strong effect on triplex stability. Their stabilizing ability can also be explained by the ion-water model. Thus, for these organic cations $V_{caged}$ is dominant, and in this case water "structure-making" occurs as a result of the hydrophobic cation. That is, the organic cation (kosmotrope) interacts much less strongly with water, and in so doing orders the water molecules around them (the effect on the interfacial water surrounding the nonpolar substance is that it becomes more ordered).

For the triplex $d(C^+-T)_6:d(A-G)_6\cdot d(C-T)_6$ at pH 7.0:

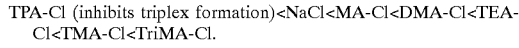

For the triplex $d(T)_{21}:d(A)_{21}\cdot d(T)_{21}$ at pH 7.0, the highest obtainable Tm is 72° C. in 5.0 M NaCl, while the highest obtainable Tm is 95° C. in 6.0 M TMA-Cl.

As both triplexes and duplexes have a high negative charge density, they are stabilized in turn by cations of positive charge density. Therefore, although $V_{caged}$ is negative for the organic cations, $TMA^+$ ($-21$ $cm^3$ $mole^{-1}$), $TEA^+$ ($-18$ $cm^3$ $mole^{-1}$), and $TPA^+$ ($-24$ $cm^3$ $mole^{-1}$), (because of their water structure-making nature, i.e., decreased volume), $TPA^+$ must not have sufficient positive charge density. Thus, it is likely that the size (and hence charge density) of these organic cations also plays a role in their tendency to stabilize triplexes. At pH 7.0 they all have one positive charge and therefore their charge density will scale with their surface area (calculated using ChemPlus in Hyperchem (HyperChem 4.0 (1994) Hypercube Corp., Waterloo, Ontario, Canada)): $MA^+$ (178 Å$^2$), $DMA^+$ (208 Å$^2$), $TriMA^+$ (232 Å$^2$) $TMA^+$ (252 Å$^2$), $TEA^+$ (325 Å$^2$), and $TPA^+$ (383

Å$^2$). This implies that TriMA$^+$ and TMA$^+$ have the optimum size and charge density to stabilize triplexes with homopyrimidine third strands. However, as observed, their decreasing charge density also makes them less soluble in H$_2$O, and this may also have an effect.

It should be noted that TEA$^+$ and TPA$^+$ have a significant destabilizing effect on the duplex d(A-G)$_6$·d(C-T)$_6$.

Triplexes are stabilized by certain alcohols, PEG, and DMSO as follows.

For the triplex d(C+-T)$_6$:d(A-G)$_6$·d(C-T)$_6$ at pH 7.0:

MeOH<EtOH<2-PrOH<1-BuOH.

For the triplex d(T)$_{21}$:d(A)$_{21}$·d(T)$_{21}$ in 50 Vol % alcohol+ MB (0.15 M Na$^+$/0.005 M Mg$^{++}$/0.01 M cacodylate titrated to the desired pH) at pH 7.0, the rank order based on Tm values (0° C.) is:

0%, MB only (23°)<MeOH (38°)<EtOH (53°)<2-PrOH (65°).

For the triplex poly r(U:A·U) in Vol % EtOH+0.016 M NaCl at pH 7.0:

0% (26°)<10% (39°)<20% (42°)<30% (45°)<50% (53°).

For the triplex d(C$^+$-T)$_6$:d(A-G)$_6$·d(C-T)$_6$ in 20 Vol % PEG(ave. molecular weight)+MB at pH 7.0:

0%, MB only (11°)<PEG200 (18°)<PEG400 (22°)<PEG600 (24°).

For the triplex d(C$^+$-T)$_6$:d(A-G)$_6$·d(C-T)$_6$ in Vol % DMSO+MB at pH 7:

0%, MB only (11°)<10% (15°)<20% (17°)<40% (20°)<50% (27°)<60% (15°).

For the triplex d(T)$_{21}$:d(A)$_{21}$·d(T)$_{21}$ in Vol % DMSO+MB at pH 7.0:

0%, MB only (23°)<30% (34°)<40% (38°)<50% (15°).

Water-miscible neutral polar organic substances can also be classified as water structure-breaking (chaotropes) or water structure-making (kosmotropes) (see Collins and Washabaugh, Q. Rev. Biophysics (18) 323–422 (1985)). The low molecular weight alcohols are water structure-making, as is the neutral hydrophilic polymer PEG and the potent H-bond acceptor DMSO.

It would appear therefore that substances that are water structure-making enhance the stability of triplexes. Conversely, no water structure-breaking substance has been observed to enhance triplex stability. This thermodynamic model of ion-water interaction has given a thermodynamic answer. We now attempt to relate this thermodynamic understanding of how "altered water structure" may influence the conformation of DNA to the molecular mechanism for triplex formation.

The result of water-alcohol, water-PEG, or water-DMSO interaction is that it reduces the water available to hydrate other 'solutes'. This is a well known observation for DNA in water/ethanol mixtures. The higher the proportion of ethanol, the less the proportion of water available for hydration of DNA (i.e., dehydration), and in 60 to 70% ethanol there is sufficient dehydration to induce a conformational change in DNA from B to A or Z. Such conformational changes require varying degrees of unwinding the DNA, with resultant changes in rotation of the nucleotide residues from 36–45° to 30–33° in the case of B to A, and even anti to syn isomerization in the case of B to Z.

In this connection, the unwinding of duplex DNA increases in the presence of MeOH, EtOH, ethylene glycol and DMSO but not glycerol (Lee, et al., (1981) Proc. Natl. Acad. Sci. U.S.A. 78, 2838–2842). Moreover, the degree of unwinding is a continuous process in response to the concentration of organic solvent. The Vol % of organic solvent required for unwinding increases in the order: DMSO<MeOH<EtOH<ethylene glycol.

As glycerol does not enhance triplex stability, it is likely that MeOH, EtOH, 2-PrOH, PEG and DMSO all enhance triplex stability by facilitating unwinding of the duplex. In fact, it would make sense that all compounds that facilitate both a B to A/Z transition and dehydration also enhance binding of third strands that must enter the major groove of the duplex. Clearly, third strand binding must require displacement of water from the major groove of the duplex to accommodate this extra strand. This is further supported by the observation that RecA facilitates third strand binding, since the hydrophobic environment created by the protein must facilitate removal of water (Iyer, et al., J. Biol. Chem. 270, 14712–717 (1995)).

Thus, it appears that substances that are water structure-making enhance the stability of triplexes. They may do so by two associated mechanisms: by facilitating the unwinding of the duplex to the extent needed to accommodate the third strand, which need not necessarily involve a B to A transition, and by facilitating the removal of water from the major groove to permit third strand binding.

EXAMPLES

To illustrate the various aspects and processes of the invention, the effects of different additives on the stability of three different triplexes is documented below. It is understood that these examples are not intended to limit the scope of the invention and that other embodiments of the invention will be apparent from the information provided to those of ordinary skill in the art.

Example 1 d(C$^+$-T)$_6$: [d(A-G)$_6$·d(C-T)$_6$]

d(A-G)$_6$ and d(C-T)$_6$ were synthesized, purified and analyzed as described in Lavelle and Fresco, Nucleic Acids Res. 23, No. 14, 2692–2705 (1995). Briefly, the strands were synthesized using standard phosphoramidite chemistry on an Applied Biosystems 380B synthesizer. The oligomers were purified by reverse phase HPLC (0.1 M triethylammonium acetate pH 7.0/acetonitrile) and ion exchange HPLC (5 M urea/20 mM sodium phosphate pH 6.0, 5 M urea/20 mM sodium phosphate/1 M sodium sulfate pH 6.0) and desalted by reverse phase chromatography using C18 Sep-Pak. Molar extinction coefficients determined after phosphodiesterase I digestion, $\epsilon_{260}$=9890 for d(A-G)$_6$ and $\epsilon_{260}$=8510 for d(C-T)$_6$ at 25° C. in 2.6×10$^{-5}$ M Tris pH 7.4/2.4×10$^{-5}$ M MgCl$_2$, were used to determine oligomer concentration. The triplex mixture was made with equimolar stocks of the two strands; after forming the duplex, a stoichiometric amount of the third strand was added (which is the same as the homopyrimidine strand of the core duplex in this case).

Absorption spectra and thermal melting profiles were determined in a computer driven AVIV 14DS spectrophotometer equipped with a thermoelectrically controlled cell holder for cells of 1 cm pathlength. Filtered, dry air was passed through the cell compartment to prevent condensation on the cell walls at low temperatures. The flow rate was set low enough so as not to create a temperature gradient between the sample and the cell holder, which was confirmed by monitoring the temperature in the sample and cell holder during trial melting profiles. For melting experiments, spectra were measured every 1 nm and 2° C.

Only triplex and duplex transitions that occur between 0 and 100° C. were observed. Care was taken to obtain true equilibrium melting profiles by recording scans only after a cuvette was allowed to reach the desired temperature (8 min). This ensured that the rate of temperature rise is less than the rate of the association-dissociation reaction under study, as confirmed by the absence of further absorbance change on longer incubation at some fixed temperature within the transition. These spectra were used to obtain melting profiles and their derivatives at appropriate wavelengths, from which melting transition temperatures. The values were obtained from the midpoint of the transition. Tm values ($T_m \pm 0.5°$ C.) were obtained by measuring each melting profile at least twice. Unless otherwise stated, Tm and % hypochromicity values were obtained from melting profiles at 260 nm. All UV-melting profiles, wavelength scans and difference spectra are plotted using raw data. % Hypochromicity was calculated using:

$$\frac{A_{260}(\text{duplex} + \text{coil}) - A_{260}(\text{triplex})}{A_{260}(\text{duplex} + \text{coil})} \times 100$$

for $3 \rightarrow 2 + 1$ transitions; and $$\frac{A_{260}(\text{coil}) - A_{260}(\text{triplex})}{A_{260}(\text{coil})} \times 100$$

for $3 \rightarrow 1 + 1 + 1$ transitions.

The effect of various additives on triplex stability was determined, and the results are presented below in Tables 1-1 to 1-28. These results were obtained at pH 7 unless otherwise noted. The abbreviation "MB" denotes a mixing buffer comprised of 0.15 M NaCl, 0.005 M $MgCl_2$ and 0.01 M cacodylate, titrated to the desired pH.

TABLE 1-1

Methylammonium chloride (MA-Cl)

| Molarity | 1st Transition | | 2nd Transition | |
|---|---|---|---|---|
| | Tm °C. | Hypochromicity % | Tm °C. | Hypochromicity % |
| 1.0 | 18 | 13 | 53 | 8 |
| 2.0 | 19 | 12 | 53 | 8 |
| 3.0 | 20 | 13 | 52 | 6 |
| 4.0 | 19 | 11 | 51 | 8 |

TABLE 1-2

Dimethylammonium chloride (DMA-Cl)

| Molarity | 1st Transition | | 2nd Transition | |
|---|---|---|---|---|
| | Tm °C. | Hypochromicity % | Tm °C. | Hypochromicity % |
| 1.0 | 20 | 11 | 53 | 8 |
| 2.0 | 23 | 10 | 52 | 8 |
| 3.0 | 26 | 9 | 51 | 6 |
| 4.0 | 27 | 10 | 49 | 8 |

TABLE 1-3

Trimethylammonium chloride (TriMA-Cl)

| Molarity | 1st Transition | | 2nd Transition | |
|---|---|---|---|---|
| | Tm °C. | Hypochromicity % | Tm °C. | Hypochromicity % |
| 1.0 | 28 | 10 | 52 | 6 |
| 2.0 | 36 | 9 | 52 | 7 |
| 3.0 (pH 3.7) | 72 (a) | 19 | — | — |
| 3.0 (pH 4.9) | 67 (a) | 15 | — | — |
| 3.0 (pH 5.8) | 58 (a) | 15 | — | — |
| 3.0 | 50 (a) | 17 | — | — |
| 3.0 M (pH 7.4) | 36 | 8 | 51 | 7 |
| 3.0 M (pH 7.8) | — | — | 52 | 8 |
| 4.0 M | 53 (a) | 16 | — | — |
| 4.0 M (pH 7.4) | 36 | 8 | 50 | 6 |

(a) Tm for a $3 \rightarrow 1$ transition.

TABLE 1-4

Tetramethylammonium chloride (TMA-Cl)

| Molarity | 1st Transition | | 2nd Transition | |
|---|---|---|---|---|
| | Tm °C. | Hypochromicity % | Tm °C. | Hypochromicity % |
| 1.0 | 31 | 10 | 54 | 9 |
| 2.0 | 29 | 9 | 55 | 7 |
| 3.0 (pH 3.7) | 75 (a) | 18 | — | — |
| 3.0 (pH 4.9) | 72 (a) | 16 | — | — |
| 3.0 (pH 5.8) | 61 (a) | 14 | — | — |
| 3.0 | 30 | 10 | 56 | 9 |
| 4.0 | 43 | 9 | 59 | 7 |
| 6.0 | 50 (a) | 23 | — | — |
| 6.0 (pH 6.0) | 67 (a) | 23 | — | — |

(a) Tm for a $3 \rightarrow 1$ transition.

TABLE 1-5

Tetraethylammonium chloride (TEA-Cl)

| Molarity | 1st Transition | | 2nd Transition | |
|---|---|---|---|---|
| | Tm °C. | Hypochromicity % | Tm °C. | Hypochromicity % |
| 0.5 | 16 | 10 | 43 | 6 |
| 1.0 | 22 | 13 | 43 | 10 |
| 1.6 | 26 | 9 | 37 | 7 |
| 2.0 | insoluble | | | |

TABLE 1-6

Tetrapropylammonium chloride (TPA-Cl)

| Molarity | 1st Transition | | 2nd Transition | |
|---|---|---|---|---|
| | Tm °C. | Hypochromicity % | Tm °C. | Hypochromicity % |
| 0.1 | — | — | 29 | 8 |
| 0.5 | — | — | 31 | 8 |
| 0.9 | — | — | 28 | 8 |
| 0.9 (pH 8.5) | — | — | 27 | 8 |
| 1.0 | insoluble | | | |

TABLE 1-7

Cetyltrimethylammonium chloride (CTriMA-Cl)

| | 1st Transition | | 2nd Transition | |
|---|---|---|---|---|
| Wt % | Tm °C. | Hypochromicity % | Tm °C. | Hypo-chromicity % |
| $10^{-4}$ | — | — | 20 | 10 |
| $10^{-3}$ | — | — | 23 (a) | 5 |
| $10^{-2}$ | 28 (b) | 5 | — | — |
| $10^{-1}$ | insoluble, micelle formation | | | |
| $10^{-4}$ + MB | 10 | 11 | 50 | 13 |
| $10^{-3}$ + MB | 22 (c) | 8 | 52 | 14 |
| $10^{-2}$ + MB | insoluble, micelle formation | | | |
| $10^{-3}$ + MB + 0.02 M TMA | 12 | 8 | 51 | 10 |
| $10^{-3}$ + MB + 0.1 M TMA | 14 | 11 | 51 | 9 |
| $10^{-3}$ + MB + 0.2 M TMA | 15 | 10 | 52 | 8 |
| $10^{-3}$ + MB + 0.4 M TMA | 16 | 11 | 52 | 8 |
| $10^{-2}$ + MB + 0.1 M TMA | 45 | 11 | 64 | 11 |
| $10^{-2}$ + MB + 0.2 M TMA | insoluble, micelle formation | | | |

(a) Tm for duplex melting.
(b) Tm 3 → 2 + 1 transition; phase transition of CTriMA masks duplex transition.
(c) very broad transition (3–40° C.).

TABLE 1-8

Tridodecylmethylammonium chloride (Tridodecyl MA-Cl)

| | 1st Transition | | 2nd Transition | |
|---|---|---|---|---|
| Wt % | Tm °C. | Hypochromicity % | Tm °C. | Hypochromicity % |
| $10^{-4}$ | — | — | 20 | 10 |
| $10^{-3}$ | — | — | 20 | 10 |
| $10^{-3}$ (f) | 41 (d) | 14 | — | — |
| $10^{-2}$ | insoluble, micelle formation | | | |
| $10^{-4}$ + MB | 10 | 10 | 51 | 11 |
| $10^{-3}$ + MB | 11 | 9 | 51 | 10 |
| $10^{-2}$ + MB | insoluble, micelle formation | | | |

(d) Tm for a 3 → 1 transition.
(f) pH 6.0.

TABLE 1-9

2,3-dioleyloxy-N-[2(sperminecarboxamido)ethyl]-N,N-dimethyl-1-propanaminium trifluoroacetate (DOSPA)

| | 1st Transition | | 2nd Transition | |
|---|---|---|---|---|
| Wt % | Tm °C. | Hypochromicity % | Tm °C. | Hypochromicity % |
| $10^{-4}$ | — | — | 21 | 11 |
| $10^{-4}$ (f) | 40 (d) | 10 | — | — |
| $10^{-3}$ | 22 (d) | 7 | — | — |
| $10^{-3}$ (f) | 40 | 6 | 79 | 7 |
| $10^{-2}$ | 27 | 6 | 77 | 25 (e) |
| $10^{-1}$ | insoluble, micelle formation | | | |
| $10^{-4}$ + MB | 10 | 11 | 50 | 16 |
| $10^{-3}$ + MB | 12 | 7 | 50 | 15 |
| $10^{-2}$ + MB | insoluble, micelle formation | | | |

(d) Tm for a 3 → 1 transition.
(e) significant overlap with phase transition of DOSPA.
(f) pH 6.0.

TABLE 1-10

Sodium Dodecylsulfate (SDS)

| | 1st Transition | | 2nd Transition | |
|---|---|---|---|---|
| Wt % | Tm °C. | Hypochromicity % | Tm °C. | Hypochromicity % |
| 0.1 + MB | — (a) | — | 51 | 12 |
| 1 + MB | — (a) | — | 51 | 11 |
| 10 + MB | — (a) | — | 54 | 12 |

(a) appears to inhibit triplex formation; however, any transitions below 20° C. are not observable as the solution solidifies ≦20° C.

TABLE 1-11

Tetramethylammonium Sulfate (TMA-S)

| | 1st Transition | | 2nd Transition | |
|---|---|---|---|---|
| Molarity | Tm °C | Hypochromicity % | Tm °C | Hypochromicity % |
| 0.1 | 16 | 7 | 48 | 21 |
| 0.5 | 20 | 17 | 56 | 11 |
| 1.0 | 25 | 14 | 57 | 11 |
| 1.5 | TMA-S precipitates | | | |

TABLE 1-12

Trehalose

| | 1st Transition | | 2nd Transition | |
|---|---|---|---|---|
| Molarity | Tm °C | Hypochromicity % | Tm °C | Hypochromicity % |
| 0.75 + MB | 12 | 7 | 47 | 10 |
| 1.5 + MB | 12 | 4 | 44 | 10 |
| 2.0 + MB | 13 | 4 | 41 | 9 |

TABLE 1-13

Glycerol

| | 1st Transition | | 2nd Transition | |
|---|---|---|---|---|
| Vol % | Tm °C | Hypochromicity % | Tm °C | Hypochromicity % |
| 10 + MB | 11 | 9 | 49 | 10 |
| 20 + MB | 12 | 9 | 45 | 10 |
| 30 + MB | 12 | 6 | 42 | 12 |
| 30 + MB + 1.0 M TriMA | 19 | 8 | 45 | 9 |

TABLE 1-14

Poly(ethylene glycol) (PEG)

| | 1st Transition | | 2nd Transition | |
|---|---|---|---|---|
| Vol %/(MW) | Tm °C | Hypochromicity % | Tm °C | Hypochromicity % |
| 20 (200) + MB | 18 | 11 | 44 | 10 |
| 40 (200) + MB | 33 (b) | 23 | — | — |
| 20 (400) + MB | 22 | 22 | 48 | 17 |
| 20 (600) + MB | 24 | 15 | 49 | 14 |

(b) Tm for a 3 → 1 transition.

TABLE 1-15

Dimethyl Sulfoxide (DMSO)

| Vol % | 1st Transition Tm °C | 1st Transition Hypochromicity % | 2nd Transition Tm °C | 2nd Transition Hypochromicity % |
|---|---|---|---|---|
| 10 + MB | 15 | 12 | 48 | 12 |
| 20 + MB | 17 | 11 | 45 | 12 |
| 40 + MB | 20 | 12 | 41 | 12 |
| 50 + MB | 27 (b) | 17 | — | — |
| 60 + MB | 15 (b) | 12 | — | — |
| 60 + MB (f) | 36 (b) | 24 | — | — |

(b) Tm for a 3 → 1 transition.
(f) pH 6.0.

TABLE 1-16

Mixing Buffer (0.15 M NaCl; 0.005 M MgCl$_2$)

| pH | 1st Transition Tm °C | 1st Transition Hypochromicity % | 2nd Transition Tm °C | 2nd Transition Hypochromicity % |
|---|---|---|---|---|
| 4.2 | 32 | 9 | 62 | 13 |
| 5.0 | 29 | 12 | 50 | 9 |
| 7.0 | 11 | 12 | 50 | 10 |
| 7.5 | 1 | 4 | 50 | 10 |

TABLE 1-17

NaCl

| Molarity | 1st Transition Tm °C | 1st Transition Hypochromicity % | 2nd Transition Tm °C | 2nd Transition Hypochromicity % |
|---|---|---|---|---|
| 0.4 | 7 | 7 | 53 | 12 |
| 0.5 | 8 | 14 | 54 | 10 |
| 0.8 | 10 | 16 | 56 | 11 |
| 0.9 | 10 | 17 | 56 | 11 |
| 1.0 | 9 | 17 | 54 | 12 |
| 2.0 | 7 | 13 | 54 | 12 |
| 3.0 | 5 | 2 | 57 | 7 |
| 5.0 | — | — | 51 | 10 |
| 6.0 | NaCl crystallizes | | | |

TABLE 1-18

Na$_2$HPO$_4$

| Molarity | 1st Transition Tm °C | 1st Transition Hypochromicity % | 2nd Transition Tm °C | 2nd Transition Hypochromicity % |
|---|---|---|---|---|
| 0.4 | 8 | 9 | 54 | 12 |
| 0.8 | 12 | 11 | 56 | 11 |
| 2.0 | 15 | 11 | 57 | 11 |
| 2.0 (pH 6.5) | 29 | 14 | 59 | 11 |
| 3.0 | Na$_2$HPO$_4$ crystallizes | | | |

TABLE 1-19

Sodium Acetate

| Molarity | 1st Transition Tm °C | 1st Transition Hypochromicity % | 2nd Transition Tm °C | 2nd Transition Hypochromicity % |
|---|---|---|---|---|
| 0.4 | 9 | 12 | 53 | 11 |
| 0.8 | 12 | 12 | 56 | 11 |
| 2.0 | 15 | 13 | 55 | 11 |
| 3.0 | 16 | 13 | 54 | 12 |

TABLE 1-20

Sodium Sulfate

| Molarity | 1st Transition Tm °C | 1st Transition Hypochromicity % | 2nd Transition Tm °C | 2nd Transition Hypochromicity % |
|---|---|---|---|---|
| 0.4 | 14 | 12 | 54 | 10 |
| 0.8 (pH 7.2) | 9 | 8 | 56 | 11 |
| 0.8 | 17 | 13 | 55 | 12 |
| 2.0 | 21 | 14 | 58 | 11 |
| 3.0 | crystallizes | | | |

TABLE 1-21

Sodium Perchlorate

| Molarity | 1st Transition Tm °C | 1st Transition Hypochromicity % | 2nd Transition Tm °C | 2nd Transition Hypochromicity % |
|---|---|---|---|---|
| 2.0 | — | — | 42 | 11 |
| 2.0 (pH 6.0) | 18 | 12 | 43 | 10 |

TABLE 1-22

Ammonium Chloride

| Molarity | 1st Transition Tm °C | 1st Transition Hypochromicity % | 2nd Transition Tm °C | 2nd Transition Hypochromicity % |
|---|---|---|---|---|
| 0.4 | 8 | 5 | 56 | 12 |
| 0.8 | — | — | 54 | 12 |
| 2.0 | — | — | 58 | 12 |

TABLE 1-23

Ammonium Sulfate

| Molarity | 1st Transition Tm °C | 1st Transition Hypochromicity % | 2nd Transition Tm °C | 2nd Transition Hypochromicity % |
|---|---|---|---|---|
| 0.4 | 8 | 4 | 55 | 12 |
| 0.8 | 19 | 13 | 57 | 12 |
| 2.0 | 28 | 13 | 58 | 11 |
| 3.0 | 37 (b) | 14 | 60 (b) | 10 |

(b) overlapping transitions.

TABLE 1-24

Methanol (MeOH)

| | 1st Transition | | 2nd Transition | |
|---|---|---|---|---|
| % MeOH | Tm °C. | Hypochromicity % | Tm °C. | Hypochromicity % |
| 10% + MB | 15 | 13 | 51 | 11 |
| 20% + MB | 15 | 14 | 48 | 11 |
| 30% + MB | 15 | 12 | 44 | 12 |
| 60% + MB | 16 | 7 | 37 | 7 |
| 70% + MB | 16 | 7 | 35 | 7 |
| 80% + MB | no transitions observed | | | |

TABLE 1-25

Ethanol (EtOH)

| | 1st Transition | | 2nd Transition | |
|---|---|---|---|---|
| % EtOH | Tm °C. | Hypochromicity % | Tm °C. | Hypochromicity % |
| 10% + MB | 12 | 12 | 48 | 10 |
| 20% + MB | 13 | 12 | 44 | 11 |
| 30% + MB | 15 | 6 | 41 | 11 |
| 40% + MB | 15 | 7 | 36 | 10 |
| 50% + MB | 21 | 23 | 38 | 8 |
| 60% + MB | 40 (a), (c) | 31 | — | — |
| 70% + MB | no transitions observed | | | |
| 50% + 1.5 M TriMA | 30 (c) | 16 | — | — |

(a) broad transition (20–60° C.).
(c) Tm for a 3 → 1 transition.

TABLE 1-26

2-Propanol (2-PrOH)

| | 1st Transition | | 2nd Transition | |
|---|---|---|---|---|
| % Propanol | Tm °C. | Hypochromicity % | Tm °C. | Hypochromicity % |
| 5% + MB | 9 | 7 | 49 | 7 |
| 10% + MB | 11 | 14 | 47 | 12 |
| 20% + MB | 17 | 9 | 43 | 13 |
| 30% + MB | 20 | 11 | 40 | 12 |
| 40% + MB | 27 (b) | 31 | 39 (b) | 15 |
| 50% + MB | 40 (c) | 38 | — | — |
| 60% + MB | insoluble | | | |
| 30% + 20% EtOH + 3 M TMA | 32 (c) | 10 | — | — |
| 40% + 3 M TMA | phase separation | | | |
| 50% + 3 M TMA | insoluble | | | |

(b) overlapping transitions.
(c) Tm for a 3 → 1 transition.

TABLE 1-27

1-Butanol (BuOH)

| | 1st Transition | | 2nd Transition | |
|---|---|---|---|---|
| % BuOH | Tm °C. | Hypochromicity % | Tm °C. | Hypochromicity % |
| 0.1% + MB | 8 | 10 | 51 | 9 |
| 1% + MB | 7 | 9 | 50 | 9 |

TABLE 1-27-continued

1-Butanol (BuOH)

| | 1st Transition | | 2nd Transition | |
|---|---|---|---|---|
| % BuOH | Tm °C. | Hypochromicity % | Tm °C. | Hypochromicity % |
| 5% + MB | 7 | 10 | 47 | 9 |
| 10% + MB | phase separation | | | |

Example 2

$d(T)_{21}:[d(A)_{21} \cdot d(T)_{21}]$

Triplexes were formed and tested as in Example 1, except that the strands $d(T)_{21}$ and $d(A)_{21}$ were used instead of $d(A-G)_6$ and $d(C-T)_6$. The concentrations of these strands were calculated using the molar extinction coefficients for poly (dA) ($\epsilon_{257}=8600$) and for poly (dT) ($\epsilon_{265}=8700$) at 25° C. The results are shown below in Tables 2-1 to 2-10.

TABLE 2-1

NaCl

| | 1st Transition | | 2nd Transition | |
|---|---|---|---|---|
| Molarity | Tm °C. | Hypochromicity % | Tm °C. | Hypochromicity % |
| 0.4 | 24 | 17 | 58 | 19 |
| 0.8 | 42 | 18 | 62 | 17 |
| 1.0 | 49 (a) | 18 | 64 (a) | 18 |
| 2.0 | 66 (b) | 33 | — | — |
| 3.0 | 70 (b) | 33 | — | — |
| 5.0 | 72 (b) | 33 | — | — |
| 6.0 | NaCl crystallizes | | | |

(a) overlapping transitions.
(b) Tm for a 3 → 1 transition.

TABLE 2-2

Ammonium Chloride

| | 1st Transition | | 2nd Transition | |
|---|---|---|---|---|
| Molarity | Tm °C. | Hypochromicity % | Tm °C. | Hypochromicity % |
| 1.0 | 65 | 36 | — | — |
| 2.0 | 71 | 36 | — | — |
| 3.0 | 76 | 36 | — | — |

TABLE 2-3

Ammonium Sulfate

| | 1st Transition | | 2nd Transition | |
|---|---|---|---|---|
| Molarity | Tm °C. | Hypochromicity % | Tm °C. | Hypochromicity % |
| 1.0 | 71 | 36 | — | — |
| 2.0 | 83 | 36 | — | — |
| 3.0 | 93 | 36 (c) | — | — |

(c) obtained by extrapolation.

TABLE 2-4

Trimethylammonium chloride (TriMA-Cl)

| Molarity | 1st Transition Tm °C. | 1st Transition Hypochromicity % | 2nd Transition Tm °C. | 2nd Transition Hypochromicity % |
|---|---|---|---|---|
| 1.0 + MB | 45 | 16 | 61 | 11 |
| 2.0 + MB | 66 (b) | 27 | — | — |
| 3.0 + MB | 70 (b) | 26 | — | — |
| 1.0 | 39 | 17 | 63 | 18 |

(b) Tm for a 3 → 1 transition.

TABLE 2-5

Tetramethylammonium salts (TMA)

| Molarity | 1st Transition Tm °C. | 1st Transition Hypochromicity % | 2nd Transition Tm °C. | 2nd Transition Hypochromicity % |
|---|---|---|---|---|
| 1.0 TMA-Chloride | 28 | 17 | 65 | 19 |
| 6.0 TMA-Chloride | 95 (b) | 33 (c) | — | — |
| 1.0 TMA-Sulfate | 54 | 10 | 74 | 13 |
| 1.5 TMA-Sulfate | TMA-S precipitates | | | |

(b) Tm for a 3 → 1 transition.
(c) obtained by extrapolation.

TABLE 2-6

Sodium salts (all 2.0 M)

| Salt Added | 1st Transition Tm °C. | 1st Transition Hypochromicity % | 2nd Transition Tm °C. | 2nd Transition Hypochromicity % |
|---|---|---|---|---|
| $Na_2HPO_4$ | 80 (b) | 33 | — | — |
| $NaOOCCH_3$ | 66 (b) | 33 | — | — |
| $Na_2SO_4$ | 80 (b) | 33 | — | — |
| $NaClO_4$ | 44 (b) | 30 | — | — |

(b) Tm for a 3 → 1 transition.

TABLE 2-7

Alcohols (all 50 Vol %)

| Alcohol Added | 1st Transition Tm °C. | 1st Transition Hypochromicity % | 2nd Transition Tm °C. | 2nd Transition Hypochromicity % |
|---|---|---|---|---|
| Methanol + MB | 38 (a) | 38 | — | — |
| Ethanol + MB | 53 (a) | 74 | — | — |
| 2-Propanol + MB | 65 (a) | 74 | — | — |

(a) Tm for a 3 → 1 transition.

TABLE 2-8

Dimethyl Sulfoxide

| Vol % | 1st Transition TM °C. | 1st Transition Hypochromicity % | 2nd Transition TM °C. | 2nd Transition Hypochromicity % |
|---|---|---|---|---|
| 30 + MB | 34 (b) | 18 | 44 (b) | 16 |
| 40 + MB | 38 (a) | 35 | — | — |
| 50 + MB | 15 | 9 | 34 | 28 |

(a) Tm for a 3 → 1 transition.
(b) overlapping transitions.

TABLE 2-9

Poly(ethylene glycol)

| Vol % (MW) | 1st Transition Tm °C. | 1st Transition Hypochromicity % | 2nd Transition Tm °C. | 2nd Transition Hypochromicity % |
|---|---|---|---|---|
| 20 (200) + MB | 39 (a) | 25 | — | — |
| 40 (200) + MB | 41 (a) | 45 | — | — |
| 20 (600) + MB | 52 (a) | 54 | — | — |

(a) Tm for a 3 → 1 transition.

TABLE 2-10

0.15 M NaCl + 0.005 M $MgCl_2$

| 1st Transition Tm °C. | 1st Transition Hypochromicity % | 2nd Transition Tm °C. | 2nd Transition Hypochromicity % |
|---|---|---|---|
| 23 | 18 | 53 | 15 |

Example 3

Poly(rU):Poly(rA).Poly(rU)

Triplexes were formed using the strands Poly(rU) and Poly(rA) (the same samples used in the work of Broitman, et al., (1987) *Proc. Natl. Acad. Sci. U.S.A.* 84, 5120–5124). The results in Tables 3-1 to 3-4 were obtained by the standard UV melting protocols described in Example 1.

TABLE 3-1

Ethanol + 0.016 M NaCl

| Vol % EtOH | 1st Transition Tm °C. | 1st Transition Hypochromicity % | 2nd Transition Tm °C. | 2nd Transition Hypochromicity % |
|---|---|---|---|---|
| 10 | 39 (a) | 37 | — | — |
| 20 | 42 (a) | 39 | — | — |
| 30 | 45 (a) | 40 | — | — |
| 50 | 53 (a) | 54 | — | — |
| 60 | insoluble | | | |

(a) Tm for a 3 → 1 transition.

TABLE 3-2

Cetyltrimethylammonium chloride + 0.016 M NaCl

| Wt % | 1st Transition | | 2nd Transition | |
|---|---|---|---|---|
| | Tm °C. | Hypochromicity % | Tm °C. | Hypochromicity % |
| $10^{-4}$ | 27 | 16 | 40 | 20 |
| $10^{-3}$ | 38 (b) | 12 | 63 (b) | 18 |
| $10^{-2}$ | insoluble, micelle formation | | | |

(b) overlapping transitions.

TABLE 3-3

Trimethylammonium chloride + 0.016 M NaCl

| Molarity | 1st Transition | | 2nd Transition | |
|---|---|---|---|---|
| | Tm °C. | Hypochromicity % | Tm °C. | Hypochromicity % |
| 0.020 | 34 | 21 | 42 | 18 |
| 0.053 | 44 (a) | 37 | — | — |
| 0.600 | 69 (a) | 41 | — | — |

(a) Tm for a 3 → 1 transition.

TABLE 3-4

Tetramethylammonium chloride + 0.016 M NaCl

| Molarity | 1st Transition | | 2nd Transition | |
|---|---|---|---|---|
| | Tm °C. | Hypochromicity % | Tm °C. | Hypochromicity % |
| 0.020 | 31 | 18 | 40 | 17 |

TABLE 3-5

0.16 M NaCl

| 1st Transition | | 2nd Transition | |
|---|---|---|---|
| Tm °C. | Hypochromicity % | Tm °C. | Hypochromicity % |
| 26 | 17 | 40 | 23 |

We claim:

1. A method for enhancing the stability of a triplex formed from one or more nucleic acid strands in a solution in vitro, said method comprising adding to the solution either of the following:
   (a) a water structure-making substance selected from the group consisting of an organic cation other than tetramethylammonium, a cationic lipid, dimethyl sulfoxide, poly(ethylene glycol), an organic anion, and an inorganic anion; or
   (b) a combination of said water structure-making substance and an alkali or alkaline earth metal cation, a tetramethylammonium cation, or a polyamine,
wherein the concentration of the water structure-making substance in a) or b) in the solution is at least about one molar.

2. The method of claim 1 wherein the water structure-making substance comprises an organic cation other than tetramethylammonium.

3. The method of claim 2, wherein the organic cation is selected from the group consisting of methylammonium, dimethylammonium, trimethylammonium, and tetraethylammonium.

4. The method of claim 2, wherein the water structure-making substance comprises a cationic lipid.

5. The method of claim 4, wherein the cationic lipid is selected from the group consisting of cetyltrimethylammonium, tridodecylmethylammonium, and 2,3-dioleyloxy-N-[2(sperminecarboxamido)ethyl]-N,N-dimethyl-1-propanammonium.

6. The method of claim 1, wherein the water structure-making substance is selected from the group consisting of dimethyl sulfoxide and poly(ethylene glycol).

7. The method of claim 1, wherein the water structure-making substance comprises an organic anion.

8. The method of claim 7, wherein the organic anion is acetate.

9. The method of claim 1, wherein the water structure-making substance comprises an inorganic anion.

10. The method of claim 9, wherein the inorganic anion is selected from the group consisting of phosphate, sulfate, cyanate, isocyanate and isothiocyanate.

11. The method of claim 1, wherein the water structure-making substance further comprises a water-miscible organic solvent.

12. The method of claim 11, wherein the water-miscible organic solvent comprises an alcohol.

13. The method of claim 12, wherein the alcohol is selected from the group consisting of methanol, ethanol, isopropanol and 2-propanol.

14. The method of claim 1, wherein the third strand comprises DNA or RNA.

15. The method of claim 1, wherein the third strand comprises an unnatural heterocycle base substitute, a base analog, an unnatural backbone, or a substituent which strengthens binding of the third strand in the triplex.

16. A method for forming a triplex from one or more nucleic acid strands, said method comprising adding to a solution in vitro, in any order, the strand(s) and an effective amount for triplex stabilization of one of the following:
   (a) a water structure-making substance selected from the group consisting of an organic cation other than tetramethylammonium, a cationic lipid, dimethyl sulfoxide, poly(ethylene glycol), an organic anion, and an inorganic anion; or
   (b) a combination of said water structure-making substance and an alkali or alkaline earth metal cation, a tetramethylammonium cation, or a polyamine; and allowing said triplex to form,
wherein the concentration of the water structure-making substance in a) or b) in the solution is at least about one molar.

17. The method of claim 16, wherein the water structure-making substance comprises an organic cation other than tetramethylammonium.

18. The method of claim 17, wherein the organic cation is selected from the group consisting of methylammonium, dimethylammonium, trimethylammonium, and tetraethylammonium.

19. The method of claim 16, wherein the water structure-making substance comprises a cationic lipid.

20. The method of claim 19, wherein the cationic lipid is selected from the group consisting of cetyltrimethylammonium, tridodecylmethylammonium, and 2,3-dioleyloxy-N-[2(sperminecarboxamido)ethyl]-N,N-dimethyl-1-propanammonium.

21. The method of claim 16, wherein the water structure-making substance is selected from the group consisting of dimethyl sulfoxide and poly(ethylene glycol).

22. The method of claim 16, wherein the water structure-making substance comprises an organic anion.

23. The method of claim 22, wherein the organic anion is acetate.

24. The method of claim 16, wherein the water structure-making substance comprises an inorganic anion.

25. The method of claim 24, wherein the inorganic anion is selected from the group consisting of phosphate and sulfate.

26. The method of claim 16, wherein the water structure-making substance further comprises a water-miscible organic solvent.

27. The method of claim 26, wherein the water-miscible organic solvent comprises an alcohol.

28. The method of claim 27, wherein the alcohol is selected from the group consisting of methanol, ethanol, isopropanol and 2-propanol.

29. The method of claim 16, wherein the third strand comprises DNA or RNA.

30. The method of claim 16, wherein the third strand comprises an unnatural heterocycle base substitute, a base analog, an unnatural backbone, or a substituent which strengthens binding of the third strand in the triplex.

31. The method of claim 1, wherein the water structure-making substance enhances triplex stability in part by effectively decreasing the amount of water at the site of triplex formation and facilitating partial unwinding of the target duplex.

32. The method of claim 16, wherein the water structure-making substance enhances triplex formation in part by effectively decreasing the amount of water at the site of triplex formation and facilitating partial unwinding of the target duplex.

* * * * *